(12) United States Patent
Romo

(10) Patent No.: US 12,708,541 B2
(45) Date of Patent: Aug. 18, 2026

(54) CUSTOMIZED ORTHOSIS WITH INTERWOVEN INTEGRATED COMPONENTS

(71) Applicant: Aspen Medical Products, LLC, Irvine, CA (US)

(72) Inventor: Harry Duane Romo, Pahrump, NV (US)

(73) Assignee: Aspen Medical Products, LLC, Irvine, CA (US)

( * ) Notice: Subject to any disclaimer, the term of this patent is extended or adjusted under 35 U.S.C. 154(b) by 295 days.

(21) Appl. No.: 18/448,924

(22) Filed: Aug. 12, 2023

(65) Prior Publication Data

US 2025/0049604 A1 Feb. 13, 2025

(51) Int. Cl.
*A61F 5/02* (2006.01)
*A61F 5/01* (2006.01)

(52) U.S. Cl.
CPC .............. *A61F 5/0111* (2013.01); *A61F 5/02* (2013.01)

(58) Field of Classification Search
CPC .... A61F 5/02; A61F 5/01; A61F 5/022; A61F 5/024; A61F 5/026; A61F 5/028; A61F 5/03
See application file for complete search history.

(56) References Cited

U.S. PATENT DOCUMENTS 3,286,277 A 11/1966 Weiss
4,240,415 A 12/1980 Wartman
4,483,333 A 11/1984 Wartman
4,745,912 A 5/1988 McMurray
6,092,622 A 7/2000 Hiers et al.
6,093,161 A 7/2000 Maeyen et al.
6,267,743 B1 7/2001 Bodenschatz et al.
(Continued)

FOREIGN PATENT DOCUMENTS

CN 1190177 C 2/2005
CN 214128973 U 9/2021
(Continued)

OTHER PUBLICATIONS

U.S. Appl. No. 17/673,716, filed Feb. 16, 2022 Non-Final Office Action dated May 5, 2025.
(Continued)

*Primary Examiner* — Victoria Hicks Fisher
(74) *Attorney, Agent, or Firm* — Rutan & Tucker, LLP

(57) ABSTRACT

One embodiment relates to an orthopedic precast comprises an interwoven shell portion and an interwoven flexible portion. Heat or other hardening agent is used to harden the shell portion, while retaining flexibility in the flexible portion. Contemplated hardening agents include light, heat, and chemical polymerizing agents. In some embodiments the shell portion includes thermoplastic threads or yarns, which is then hardened by heating the thermoplastic sufficiently to at least partially melt, and thereby fuse together some of the threads or yarns, and then cooling to ambient temperature for enhanced rigidity. In other embodiments, the precast is contained in a bag or other airtight container, along with a self-heating composition that is triggered to release heat upon contact with oxygen. In still other embodiments, the precast includes a prepolymer of other polymerizable composition, which is polymerized by effective application of light, heat, and/or chemical agent(s) or deployed as a wearable.

10 Claims, 6 Drawing Sheets

(56) References Cited

U.S. PATENT DOCUMENTS

| | | | |
|---|---|---|---|
| 7,905,848 | B2 | 3/2011 | Cuypers et al. |
| 8,303,527 | B2 | 11/2012 | Joseph |
| 8,480,604 | B2 | 7/2013 | Messer |
| 8,959,959 | B1 | 2/2015 | Podhajny |
| 9,295,575 | B1 | 3/2016 | Dignam et al. |
| 9,452,073 | B2 | 9/2016 | Cuypers et al. |
| 9,572,703 | B2 | 2/2017 | Matthews |
| 10,081,889 | B2 | 9/2018 | Cuypers et al. |
| 10,343,309 | B2 | 7/2019 | Cuypers et al. |
| 10,750,826 | B2 | 8/2020 | Meythaler et al. |
| 10,765,773 | B2 | 9/2020 | Watson |
| 10,864,099 | B2 | 12/2020 | Cuypers et al. |
| 11,964,061 | B2 | 4/2024 | Romo, Jr. et al. |
| 12,433,776 | B2 | 10/2025 | Damstra et al. |
| 2002/0088501 | A1 | 7/2002 | Bruner |
| 2002/0182961 | A1 | 12/2002 | Clercq et al. |
| 2003/0224685 | A1 | 12/2003 | Sharma |
| 2004/0118018 | A1 | 6/2004 | Dua |
| 2006/0253960 | A1 | 11/2006 | Horn et al. |
| 2010/0199520 | A1 | 8/2010 | Dua et al. |
| 2012/0210488 | A1 | 8/2012 | Blakely et al. |
| 2013/0025075 | A1 | 1/2013 | Meschter et al. |
| 2013/0260629 | A1 | 10/2013 | Dua et al. |
| 2014/0213953 | A1 | 7/2014 | Heyd et al. |
| 2015/0121657 | A1 | 5/2015 | Ingimundarson et al. |
| 2015/0133839 | A1 | 5/2015 | Roebelt et al. |
| 2016/0286898 | A1 | 10/2016 | Manz et al. |
| 2017/0079828 | A1 | 3/2017 | Pedtke et al. |
| 2018/0085244 | A1 | 3/2018 | Burke et al. |
| 2018/0125166 | A1 | 5/2018 | Kilgore |
| 2018/0127904 | A1 | 5/2018 | Adami et al. |
| 2018/0127905 | A1 | 5/2018 | Amis et al. |
| 2018/0169963 | A1 | 6/2018 | Dua et al. |
| 2018/0317592 | A1 | 11/2018 | Rudolf et al. |
| 2018/0332920 | A1 | 11/2018 | Burch |
| 2019/0037967 | A1 | 2/2019 | McFarland, II et al. |
| 2019/0208862 | A1 | 7/2019 | Poegl et al. |
| 2019/0343216 | A1 | 11/2019 | Huffa et al. |
| 2019/0387813 | A1 | 12/2019 | Almog |
| 2020/0009288 | A1 | 1/2020 | Geremtzes et al. |
| 2020/0022457 | A1 | 1/2020 | Oordt et al. |
| 2020/0375317 | A1 | 12/2020 | Meir |
| 2021/0030117 | A1 | 2/2021 | Frazier et al. |
| 2021/0153602 | A1 | 5/2021 | Polgar et al. |
| 2022/0039991 | A1 | 2/2022 | Heronen et al. |
| 2022/0256939 | A1 | 8/2022 | Romo, Jr. et al. |
| 2022/0257824 | A1 | 8/2022 | Romo, Jr. et al. |

FOREIGN PATENT DOCUMENTS

| | | | |
|---|---|---|---|
| FR | 3018043 | A1 | 9/2015 |
| GB | 1253651 | A | 11/1971 |
| JP | H0370558 | A | 3/1991 |
| JP | 2004313385 | A | 11/2004 |
| JP | 2004339651 | A | 12/2004 |
| KR | 20170017613 | A | 2/2017 |
| WO | 99/62440 | A1 | 12/1999 |

OTHER PUBLICATIONS

U.S. Appl. No. 18/448,922, filed Aug. 12, 2023 Notice of Allowance dated Jun. 24, 2025.

EP 22756965.4 filed Sep. 18, 2023 Extended European Search Report dated Dec. 12, 2024.

PCT/US2024/041849 filed Aug. 11, 2024 International Search Report and Written Opinion dated Dec. 4, 2024.

PCT/US2024/041849 filed Aug. 11, 2024 International Search Report and Written Opinion dated Jan. 13, 2025.

PCT/US2024/041851 filed Aug. 11, 2024, International Search Report and Written Opinion dated Dec. 17, 2024.

U.S. Appl. No. 17/673,716, filed Feb. 16, 2022 Final Office Action dated Sep. 29, 2024.

U.S. Appl. No. 17/673,716, filed Feb. 16, 2022 Restriction Requirement dated Apr. 24, 2024.

U.S. Appl. No. 17/673,716, filed Feb. 16, 2022 Final Office Action dated Nov. 17, 2025.

U.S. Appl. No. 18/448,921, filed Aug. 12, 2023, Non-Final Office Action dated Dec. 18, 2025.

PCT/US2022/016874 filed Feb. 17, 2022 International Search Report and Wirtten Opinion dated Jul. 19, 2022.

U.S. Appl. No. 17/178,071, filed Feb. 17, 2021 Non-Final Office Action dated Jul. 17, 2023.

U.S. Appl. No. 17/178,071, filed Feb. 17, 2021 Notice of Allowance dated Nov. 29, 2023.

U.S. Appl. No. 17/178,071, filed Feb. 17, 2021 Restriction Requirement dated Jul. 11, 2022.

U.S. Appl. No. 17/673,716, filed Feb. 16, 2022 Non-Final Office Action dated Oct. 2, 2023.

U.S. Appl. No. 17/673,716, filed Feb. 16, 2022 Restriction Requirement dated Mar. 31, 2023.

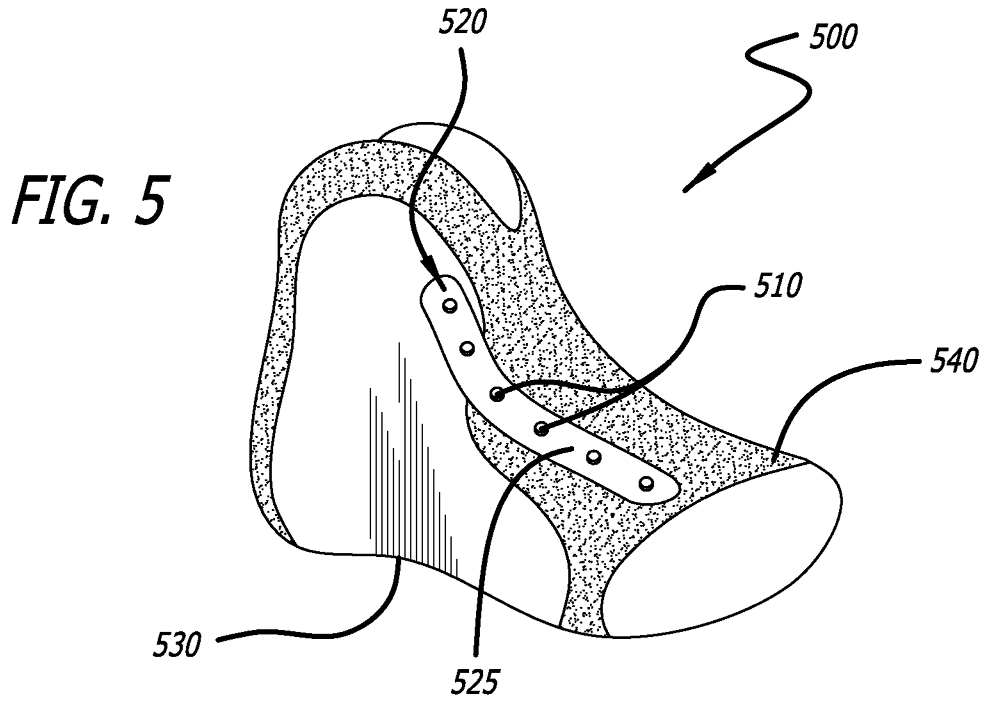
FIG. 5
520
500
510
540
530
525
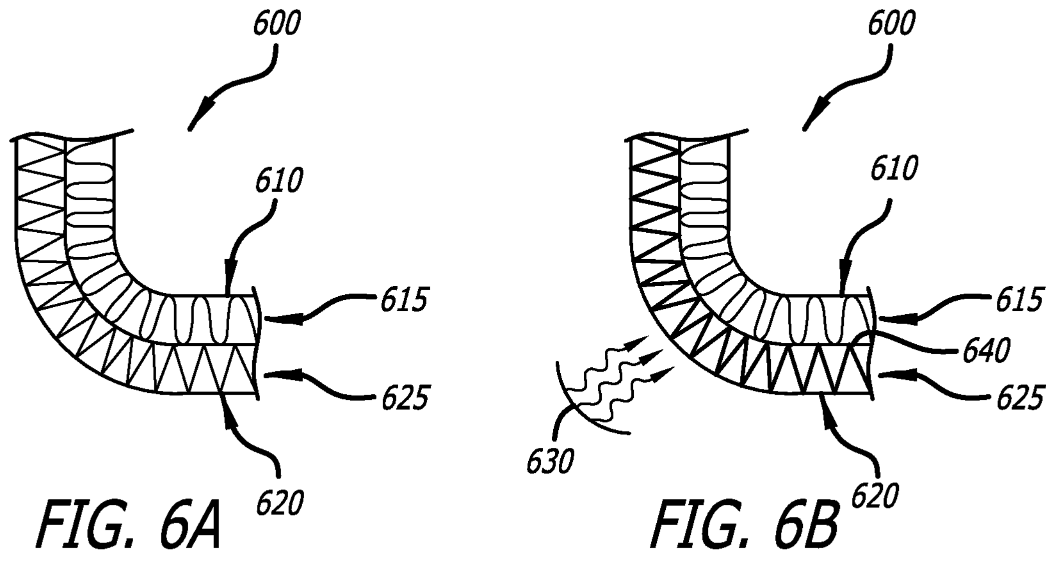
600
610
615
625
620
FIG. 6A
600
610
615
640
625
630
620
FIG. 6B

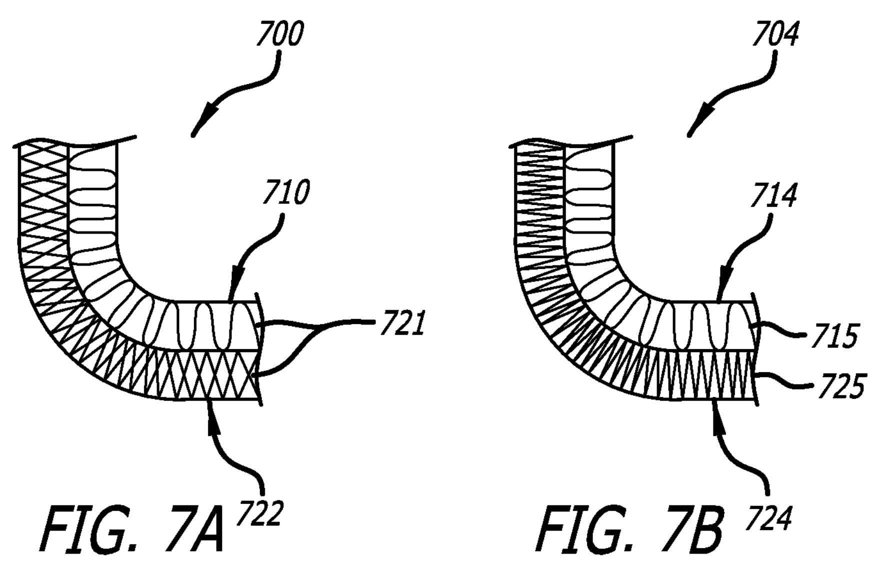
FIG. 7A
FIG. 7B
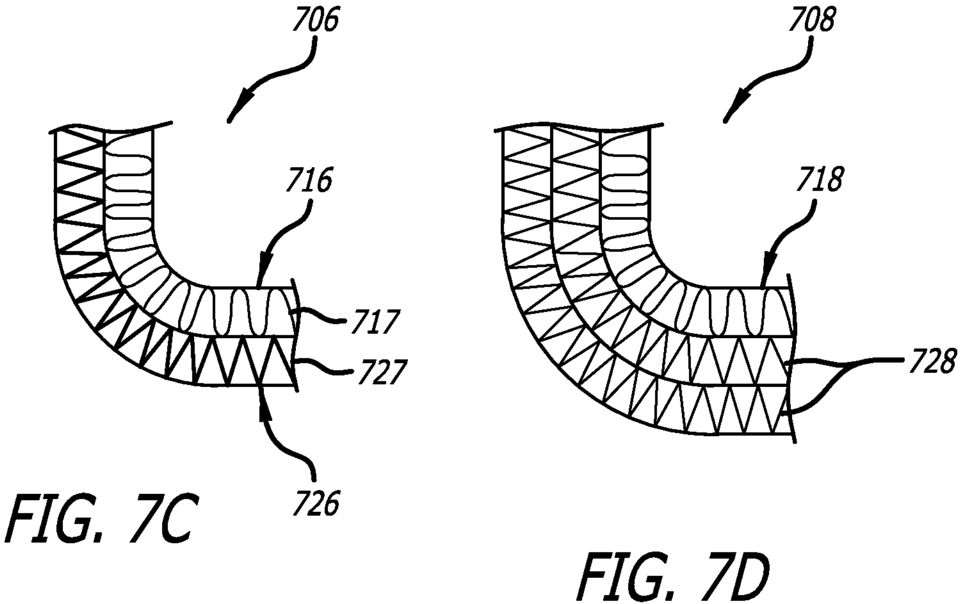
FIG. 7C
FIG. 7D

CUSTOMIZED ORTHOSIS WITH INTERWOVEN INTEGRATED COMPONENTS

FIELD

Embodiments of the invention related to one or more components interwoven within an orthopedic precast for transformation into harden components for fitting of an orthosis produced from the orthopedic precast.

BACKGROUND

The following description includes information that may be useful in understanding embodiment of the invention. It is not an admission that any of the information provided herein is prior art or relevant to the presently claimed invention, or that any publication specifically or implicitly referenced is prior art.

Orthopedic braces (orthoses) usually need to be adjusted or customized in some manner to conform to the body part(s) being braced, and then properly positioned. One type of orthosis is constructed to provide back (spinal) support, where type of "back" orthoses include a lumbar-sacral orthosis (LSO) and a thoracic-lumbar-sacral orthosis (TLSO). For instance, a TLSO is a type of back orthosis used to support and immobilize the lumbar and sacral spine regions of a patient. Inclusive of the LSO construction in combination with additional features, a TLSO provides support and stabilization of the spine normally after a back injury or to address a spinal pathology. These back orthoses include adjustment mechanisms to ensure a proper fit of the orthoses against the back area.

More specifically, conventional back orthoses are typically adjustable through the use of an adjustment mechanism integrated into each of the back orthoses, where the adjustment mechanism may be configured to supply proper compression and effectuate trunk (core) stabilization. An adjustment mechanism is a featured component within a back orthosis, as when properly fit, a back orthosis may offer stability, provide the patient with improved pain reduction, and promoted healing. If the circumference of the back orthosis is inadequate or the contours of the back orthosis cannot accommodate the user, the fit (e.g., proper compression and stabilization) will be inadequate. Inadequate fit of the back orthosis may lead to non-compliance with respect to consistent wearing of the back orthosis.

Adjustment mechanisms for an orthosis, especially a back orthosis, may be accomplished through a pulley system, fasteners, or other components integrated into the back orthoses to assist in the fitting. However, these adjustment mechanisms tend to be installed after formation of the back orthosis, and thus, the installation process is costly and time-consuming.

Thus, there is a need for systems and methods for efficiently producing custom orthoses with integrated components to avoid additional costs associated with separate design teams needed for the installation of a pulley system, fasteners, and other components that may be used to comfortably secure the orthosis to the patient.

BRIEF DESCRIPTION OF THE DRAWINGS

FIG. 5 is a perspective view of an exemplary embodiment of a post-operative shoe configured with interwoven, integrated eyelets 510 positioned within interwoven regions located above a rigid foot plate.

FIG. 6A is a schematic of an exemplary embodiment of a phase translation conducted on interwoven, integrated components within an orthopedic precast.

FIG. 6B is a schematic of the exemplary orthopedic precast portion of FIG. 6A, in which thermoplastic material associated with the interwoven, integrated components is heated and undergoes a phase change upon cooling of a partially melting thermoplastic material.

FIG. 7A is a schematic of an exemplary embodiment of a portion of an interwoven component of an orthopedic precast having a second interwoven portion configured with a higher concentration of a thermoplastic material than a first interwoven portion.

FIG. 7B is a schematic of an exemplary embodiment of a portion of an orthopedic interwoven component featuring a first and second interwoven portions configured with different interweaving patterns.

FIG. 7C is a schematic of an exemplary embodiment of an interwoven component of an orthopedic precast having a first interwoven portion configured with thinner strands of a thermoplastic material than the second interwoven portion.

FIG. 7D is a schematic of an exemplary embodiment of an interwoven component of an orthopedic precast having a second interwoven portion configured with a plurality of layers that include strands of a thermoplastic material, where the number of layers of the second interwoven portion exceed layers of a first interwoven portion.

DETAILED DESCRIPTION

Figure 1A:
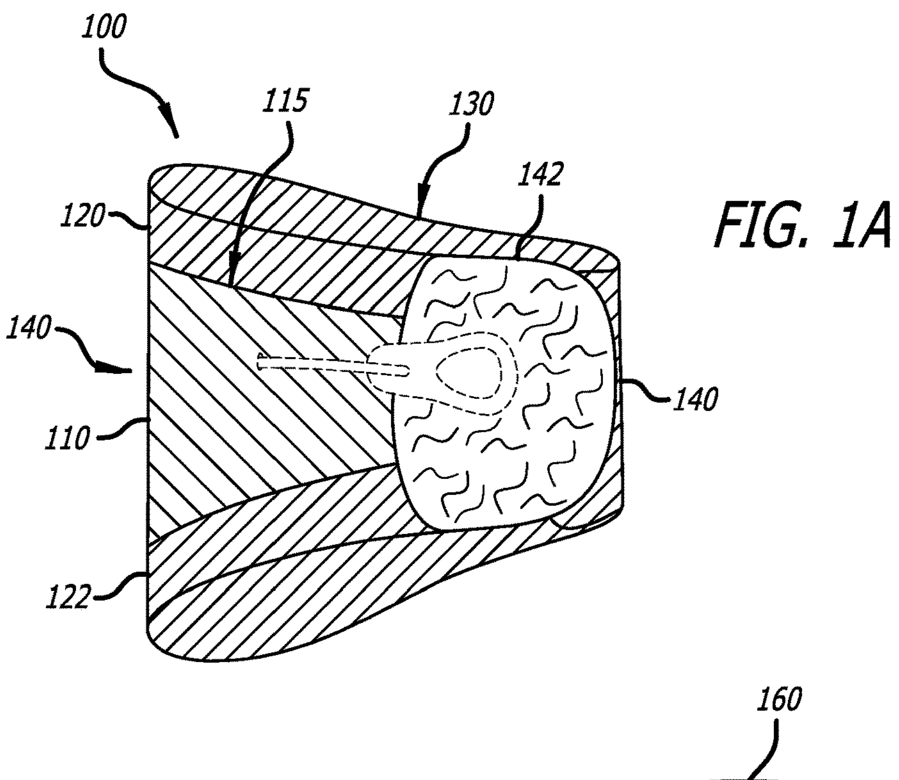
FIG. 1A is a perspective view of a first exemplary embodiment of an orthopedic precast having interwoven component forming an adjustment mechanism for a resultant back orthosis.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter may be considered to include any combination of A, B, C, and/or D, even if not explicitly disclosed.

In some embodiments, the numbers expressing quantities of ingredients, properties such as concentration, reaction conditions, and so forth, used to describe and claim certain embodiments of the invention are to be understood as being modified while still retaining the spirit and scope of the disclosed invention. Accordingly, in some embodiments, the numerical parameters set forth in the written description and attached claims are illustrative approximations that can vary depending upon the desired properties sought to be obtained by a particular embodiment.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

While each inventive aspect of the disclosure may be subject to various modifications, equivalents, and alternative forms, specific embodiments thereof have been shown by way of example in the drawings and will now be described in detail. It should be understood that each inventive aspect is not limited to the particular embodiments disclosed, but in contrast, the intention is to cover modifications, equivalents, and alternative forms of the inventive aspects within the specific embodiments as each inventive aspect may be implemented into any of these different embodiments.

I. General Summary

The inventive subject matter pertains to an orthopedic precast formed by interwoven materials that includes one or more types of thermoplastic materials having the same or different melting temperatures. As described below, the orthopedic precast includes strands of thermoplastic material that, upon an application of heat greater than its prescribed thermal threshold, undergo a phase change by partially melting but significantly retaining its original shape. Upon cooling, the thermoplastic material transitions from a flexible (fabric-like) material to a rigid material (e.g., non-bending material, material that allows for limited bending, etc.) that forms part of a resultant orthosis created from the orthopedic precast. Herein, the strands of thermoplastic material may be interwoven and layered to form components for adjustment of the resultant orthosis, such as through sizing or fastening.

The orthopedic precast is configured to produce an orthosis (or a portion of an orthosis) upon activation. According to one embodiment of the disclosure, the activation process may involve an application of a prescribed amount of heat to the orthopedic precast in order to partially melt the thermoplastic material within one or more of the interwoven portions forming the orthopedic precast. This application of heat may be accomplished by direct heating (e.g., heated air flow, heated environment, heated steam, etc.). After experiencing a phase change (i.e., transition from a first state to a second state such as from a flexible state to a rigid state), the regions of the orthopedic precast having strands of thermoplastic material are transformed into a rigid "shell" portion, which provides part of the support framework for the custom orthosis. Examples of types of orthopedic precasts may include, but are not limited or restricted the following: an ankle-foot orthosis (AFO), a cervical orthosis, a torso or back orthosis, a leg-ankle-foot orthosis, a wrist orthosis, a shoulder orthosis, or other types of orthoses.

According to one embodiment of the disclosure, the orthopedic precast features components that are interwoven as part of the material forming the orthopedic precast and designed to assist in the fitting (e.g., adjustment, fastening, etc.) of the resultant orthosis onto a wearer. For example, an interwoven "component" may include, but is not limited or restricted to a conveyance mechanism (e.g., pulley member, etc.), guided slot, fastener, or the like. Examples of a fastener may include, but are not limited or restricted to the following: snap/press stud, button, toggle, popper, buckle, grommet, or the like. Other examples of interwoven components may be directed to guides, slots, eyelets, or other components that would assist an interconnect in the tightening and/or loosening of regions of the resultant orthosis produced from the orthopedic precast.

As described below, the orthopedic precast may feature (i) a first portion including one or more interwoven strands of at least a first thermoplastic material (ii) a second portion including one or more interwoven strands of a second thermoplastic material different from the first thermoplastic material and/or including non-thermoplastic material. The second interwoven portion is attached to the first interwoven portion. In some regions of the orthopedic precast, the first interwoven portion and the second interwoven portion may be attached as part of a single layer precast construction, where these portions of the precast may utilize different material(s) and/or different interweaving techniques to provide greater rigidity or maintain a flexible and/or elastic construction. Additionally, the first interwoven portion and/or the second interwoven portion may feature regions with multiple interwoven layers of thermoplastic material that, when partially melted and cooled, produce one or more three-dimensional components with depth provided through the layering of the interwoven strands of thermoplastic material. Based on the type of thermoplastic material, the interweave pattern or strand width, these interwoven components may feature different rigidity than their surrounding areas.

When activated, these interwoven components integrated as part of the orthopedic precast may experience a phase change to become more rigid than their original construction. For example, the activation process may involve an application of a prescribed amount of heat to the orthopedic precast in order to partially melt the thermoplastic material associated with the interwoven components while significantly retaining their intended construction. When cooled, the interwoven components have transitioned from flexible interwoven patterns within the orthopedic precast into rigid components that may be used in adjustment in the fitting of the resultant orthosis.

The thermoplastic material forming the interwoven components can be a single type or a collection of different types of thermoplastic material. According to one embodiment of the disclosure, the melting temperatures of different thermoplastic materials used in the same precast may range from 80° Celsius (C) and 350° C., and differ by 10° C., 20° C., or more.

In some embodiments, the thermoplastic material composition can comprise at least 30 wt % of an orthopedic precast. For example, the thermoplastic portions of the orthopedic precast can comprise between 5 wt % and 90 wt % of its total weight, such as 50 wt % and 90 wt % of the orthopedic precast. Hence, the use of thermoplastic material is significant, where certain portions of the thermoplastic material may involve phase change operations to increase their rigidity while other portions of the thermoplastic material may retain in their original, flexible state within the resultant orthosis.

II. Terminology

As used herein, the terms "interweaving," "interweaved," "interwoven," or any other tenses thereof are generally defined as any arrangement of comprising one or more strands of material (e.g., thread, yarn, etc.) within an object (e.g., orthopedic precast) to produce a custom orthosis. The arrangement of material may include one or more types of materials attached together as a single layer of continuous material or multiple (two or more) layers of material. This attachment may occur through an interweaving process that includes knitting, stitching (e.g., "V" shaped stiches), weaving (interlacing strands of material), crocheting (knot-like stitches), macramé (knot-like stiches in geometrical patterns), and/or a topical application such as spray-on application of thermoplastic material to alter the composition of the material such as altering a non-thermoplastic material to a thermoplastic material.

Furthermore, this interweaving of material may be performed in accordance with a two-dimensional (2D) interweaving process or a three-dimensional (3D) interweaving process. The 2D interweaving process allows for the creation of a low-profile orthoses where the shell portion and flexible portion are interwoven to form a single layer of material. The 3D interweaving process may be utilized to create a layered interwoven orthosis, such as added padding and/or additional layers of the same or different types of thermoplastic material may be added to the shell portion to increase its rigidity. Also, the increased layering provides increased density for larger-sized orthoses or in certain areas of the orthoses that need increased density (e.g., hip area, etc.).

As used herein, the terms "rigid" or "rigidity" with respect to an object (e.g., orthopedic precast, resultant orthosis, etc.) or a portion of the object based on an orthopedic precast, means that the rigid object or rigid portion of the object will resist bending or deformation. According to this definition, different lengths of a given structure and composition can be rigid at a shorter length, and flexible at a longer length. As an illustrative example, in some cases, a "rigid" object or "rigid" portion(s) of the object may represent that the object or the portion of the object may be deformed, in some cases permanently (i.e., broken), if bent or twisted by a predetermined angle. For some levels of rigidity, the predetermined angle may be at least 30° end to end. For other levels of rigidity, where the object or the portion of the object may be considered to be semi-rigid, a bending or twisting over 90° (and perhaps frequent and recurrent bending or twisting) would be needed to cause deformation. As used herein, the terms "bent" or "bending" may be construed to applying an angular deformation, which may include twisting.

As used herein, the term "flexible" with respect to an object or a portion of the object may signify that the object or the object portion will not be permanently deformed by bending. For example, an interwoven portion of an orthopedic precast may be flexible in nature, even after a heating and cooling process. As used herein, the term "permanently deformed" means that deformation remains unless the deformation is actively repaired. According to this definition, the object or a portion of the object could be rigid in one direction, and flexible in another direction. Unless otherwise specified in such cases, the object or portion of the object is still deemed to be rigid.

As used herein, the term "elastic" with respect to an object or portion of the object means that if the elastic portion is stretched or compressed lengthwise by at least 10%, it will return to its resting length, without the need for application of an external force, and without permanent deformation.

As used herein, the term "shell" means a structure configured to impart rigidity that restrains movement of a part of a patient's body, wherein the structure is either (i) rigid after an application of a prescribed heating and cooling phase or (ii) will become rigid upon completion of that heating and cooling phase. In particular, an interwoven portion of an orthopedic precast existing in a non-rigid state may constitute a shell portion by having characteristics that allow this interwoven portion to transition from its non-rigid or flexible form to a rigid form in response to an application of heat (heated air, heated steam, etc.) that is equal to or exceeds a prescribed melting temperature and subsequent cooling. In some embodiments, the shell may include a structure having a cavity, hollow, or lumen.

As used herein the term "patient" includes both humans and animals, independently of whether the patient is under the care of a medical or veterinary professional.

As used herein, the term "strand" is generally defined as an elongated length of one or more natural, artificial, or combined natural and artificial substances. According to one embodiment of the disclosure, each strand may be a fiber of a prescribed width (e.g., no more than 3 millimeters (mm) thick over a length of at least one centimeter (cm), although other sizing is contemplated). Examples of a "strand" may include thread, yarn, string, cord, or any flexible material that may be organized into a structure (e.g., stitched, weaved, etc.) to produce an object such as an orthopedic precast (for transformation into an orthosis) for example. Where the strand or strands denote thermoplastic material, these strands may be elongated fibers formed with thermoplastic material, or alternatively, the strand may be another substance at least partially coated with thermoplastic material or impregnated with thermoplastic material that are still subject to phase transitions (changes).

In some embodiments, the orthopedic precast may be transformed into an orthosis having a construction that includes both shell and flexible portions. In some embodiments, the orthosis may be configured with a construction that includes shell portions of different levels of rigidity. The shell portions may be oriented lengthwise, widthwise, or crosswise, depending on the direction and degree of bending needed for the shell portion. As used herein, the term "crosswise" includes various degrees of diagonality.

As used herein, and unless the context dictates otherwise, the term "coupled to" is intended to include both direct coupling (in which two elements that are attached to and in contact with each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps, or acts are in some way inherently mutually exclusive.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed.

No language in the specification should be construed as indicating any non-claimed element essential to the practice of the invention.

Various objects, features, aspects, and advantages of the inventive subject matter will become more apparent from the following detailed description of preferred embodiments, along with the accompanying drawing figures in which like numerals represent like components.

III. Illustrative Orthopedic Precast Architectures

The following illustrations and description is directed to precast architectures that may be used to generate resultant orthoses with the same architecture. The illustrative architectures are not limited, but rather, have been selected to highlight functionality that may be deployed in any orthosis architecture.

Referring to FIG. 1A, a perspective view of a first exemplary embodiment of an orthopedic precast 100 having one or more interwoven components forming an adjustment mechanism 150 for a resultant back orthosis is shown. The orthopedic precast 100 may be configured with a first portion 110 formed of interwoven material including one or more strands of thermoplastic material. The strands of thermoplastic material are flexible in their original state during the interweaving process and are used to form interwoven components 115 within the orthopedic precast 100. These interwoven components 115 undergoes a phase change from an interwoven pattern of flexible thermoplastic material into a rigid construction after a prescribed amount of heat is applied thereto.

Featured above and below the first portion 110, upper and lower portions 120 and 122 may be interwoven with non-thermoplastic material (each referred to as an "edge portion"). As shown, for this embodiment of the disclosure, the first portion 110 and the edge portions 120, 122 generally compose a tube (e.g., belt) 130, with arms 140 and 142 at opposite ends of the tube 130 (e.g., arm 140 visible with arm 142 hidden in the folded position).

According to one embodiment of the disclosure, the interweaving of the first portion 110 and/or the edge portions 120, 122 may be oriented crosswise with respect to a direction of the belt 130 to partially restrict but retain foldability (e.g., anterior/posterior movement) of the belt 130. According to another embodiment of the disclosure, the interweaving of the first portion 110 may be oriented inferior-superior (e.g., vertically) to allow for anterior/posterior movement of the belt 130. The orientation of the interweaving of the thermoplastic material (by itself or in combination with non-thermoplastic material) within the orthopedic precast 100 results in a construction of the resultant orthosis that permits movement in certain directions and precludes or discourages movement in other directions.

Figure 1C:
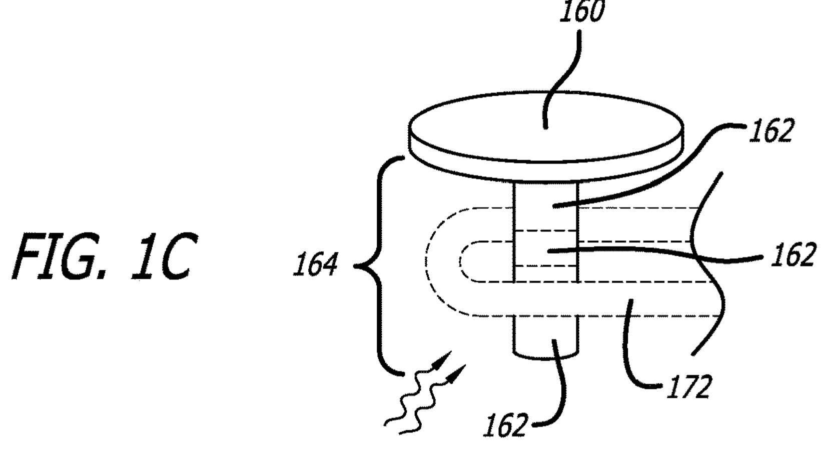
FIG. 1C is a perspective view of the resultant back orthosis formed by the orthopedic precast of FIG. 1A.

As further shown in FIG. 1A, the edge portions 120, 122 are positioned on an outer edge of the belt 130 to create a transitional area between the first portion 110 that, upon conversion of the precast 100 into the resultant orthosis, changes from a flexible material into a rigid material (hereinafter, "shell portion"). This transitional area provides a more comfortable fit and better anatomical stabilization of the resultant orthosis when worn. Also, the integration of components of the adjustment mechanism 150 within the orthopedic precast 100, where these components are interwoven in the formation of the orthopedic precast 100 and converted into a hardened state during transition of the orthopedic precast into an orthosis 195 as further shown in FIGS. 1B-1C, enable the generation of an off-the-shelf orthosis that can be customized to the patient without the orthosis requiring secondary operations to install fasteners, adjustment mechanisms and other components onto the orthosis after manufacture.

Figure 1B:
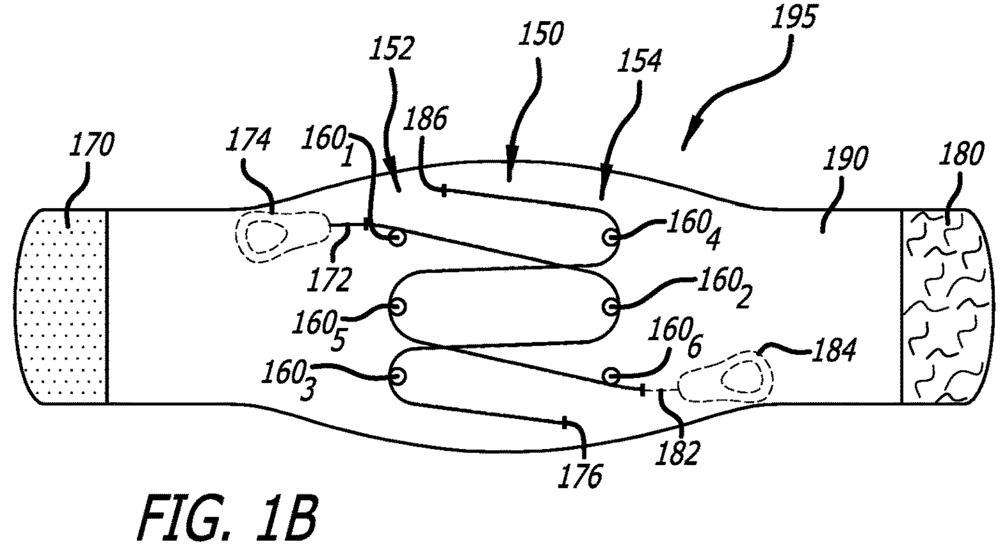
FIG. 1B is a perspective view of a pulley component of the adjustment mechanism of FIG. 1A.

Referring now to FIG. 1B, a perspective view of the components 115 of FIG. 1A partially forming the adjustment mechanism 150 is shown. Herein, the components 115 may feature a first set of pulley members 152 operating as a first pulley system and a second set of pulley members 154 operating as a second pulley system. Each pulley member $\mathbf{160_1}$, $\mathbf{160_5}$ & $\mathbf{160_3}$ of the first set of pulley members 152 and each pulley member $\mathbf{160_4}$, $\mathbf{160_2}$ & $\mathbf{160_6}$ of the second sets of pulley members 154 is formed by layered segments of strands of the thermoplastic material in an orientation to form a first pulley system inclusive of pulley members $\mathbf{160_1}$-$\mathbf{160_3}$ and a second pulley system inclusive of pulley members $\mathbf{160_4}$-$\mathbf{160_6}$.

After regions inclusive of each of pulley member $\mathbf{160_1}$-$\mathbf{160_3}$ are heated above the melting temperature of the thermoplastic material and cooled, the pulley member $\mathbf{160_1}$-$\mathbf{160_3}$ are hardened and operate as intended. As an illustration shown in FIG. 1C, each pulley member (e.g., pulley member $\mathbf{160_1}$) may be formed from layers of thermoplastic material 162 operating as post members that join to form a rigid post 164 after heat 166 is applied to partially melt the post members 162 and transform into the rigid post 164 after cooling.

Thereafter, a cord 172 may be threated and the pulley member $\mathbf{160_1}$ used for tightening of the resultant orthosis 195 of FIG. 1B based on movement of the cord 172 via the pulley member $\mathbf{160_1}$. More specifically, as shown in FIG. 1B, the pulley members $\mathbf{160_1}$-$\mathbf{160_3}$ for responsible for tightening an area associated with a first lateral arm 170 of the resultant orthosis 195 when the cord 172 with a pull handle 174 is threaded through pulley members $\mathbf{160_1}$-$\mathbf{160_3}$ with a cord stop 176 for attachment of the cord 172 to an inner surface 190 of the resultant orthosis 195.

Similarly, regions inclusive of pulley members $\mathbf{160_4}$-$\mathbf{160_6}$ may be heated above the melting temperature of the thermoplastic material forming and pulley members $\mathbf{160_4}$-$\mathbf{160_6}$ and subsequently cooled. As a result, rigid pulley members $\mathbf{160_4}$-$\mathbf{160_6}$ are formed, where the pulley members $\mathbf{160_4}$-$\mathbf{160_6}$ are responsible for tightening an area associated with a second lateral arm 180 of the resultant orthosis 195. The tightening occurs when a cord 182 with a pull handle 184 is threaded through pulley members $\mathbf{160_4}$-$\mathbf{160_6}$ with a cord stop 186 for attachment of the cord 182 to the inner surface 190 of the resultant orthosis 195.

Herein, according to one embodiment of the disclosure, strands forming the pulley members $\mathbf{160_1}$-$\mathbf{160_6}$ may include at least one type of thermoplastic material. For example, the strands forming the pulley members $\mathbf{160_1}$-$\mathbf{160_6}$ operating as a portion of the adjustment mechanism 150 may include a single type of thermoplastic material. Alternatively, the strands forming the pulley members $\mathbf{160_1}$-$\mathbf{160_6}$ may constitute a composite, which may include at least two different thermoplastic materials, where the thermoplastic materials may have the same or different melting temperatures. As yet another alternative embodiment of the disclosure, the strands forming the pulley members $\mathbf{160_1}$-$\mathbf{160_6}$ can also be a composite of one or more thermoplastic materials and one or more non-thermoplastic materials, provided the rigidity of the pulley members $\mathbf{160_1}$-$\mathbf{160_6}$ is altered after a selected temperature and duration of heat is applied and the pulley members $\mathbf{160_1}$-$\mathbf{160_6}$ are cooled. The strands of thermoplastic material(s) forming the pulley members $\mathbf{160_1}$-$\mathbf{160_6}$ may feature thermoplastic material in their entirety or may feature materials coated and/or impregnated (through an application process) with thermoplastic material. Herein, "thermoplastic material" may reference a collection of material inclusive of one or more strands of thermoplastic material that, when heated and cooled, alter the overall rigidity of the material while "non-thermoplastic material" is devoid of thermoplastic material to affect such rigidity.

According to one embodiment of the disclosure, the thermoplastic materials may be configured to form flexible strands at room temperature, are non-toxic, melt between 140° C. and 350° C., and become rigid when strands are partially melted together into a sheet or mat having a thickness of 0.5 mm to 6 mm. Contemplated examples of thermoplastic materials may include, but are not limited or restricted to the following: Polyethylene Terephthalate (PET), Polyether ether ketone (PEEK), Polyphenylene oxide (PPO), Polypropylene (PP), polyethylene (PE), polyvinyl chloride (PVC) and polystyrene (PS), poly(methyl methacrylate) (PMMA), Acrylonitrile butadiene styrene (ABS), Polylactic acid (PLA), Polybenzimidazole (PBI), Polycarbonate (PC), Polyether sulfone (PES), Polyoxymethylene (POM), Polyphenylene sulfide (PPS), Polystyrene, Polyvinyl chloride (PVC), Polyvinylidene fluoride (PVDF), Polytetrafluoroethylene (PTFE), Polyamide 6 (PA6), Polybutylene terephthalate (PBT), Polyetherimide (PEI), or the like.

The thermoplastic and non-thermoplastic materials can be selected using any combination of natural and synthetic materials to accomplish a desired characteristic, as for example, a desired degree of stiffness, compressibility, flexibility, bending, stretch, and resilience. As described above, one or more strands associated with the interwoven components, namely the pulley members $160_1$-$160_6$ may include both thermoplastic and non-thermoplastic materials. For example, the non-thermoplastic material may include Kevlar™ to increase the durability/toughness of the resultant orthosis 195, as one or more other non-thermoplastic materials (e.g., cotton fibers, non-carbon fibers, nanotubes, glass fibers, ceramic, and/or metal fibers) may be used. Similarly, one or more strands of material forming the edge portion(s) 120 and/or 122 can also comprise thermoplastic and/or non-thermoplastic materials. However, according to this embodiment of the disclosure, the thermoplastic material of the edge portion(s) 120 and/or 122 may feature a higher melting point that is substantially above the melting point of the thermoplastic material used in the first portion 110 to retain more flexibility than the first portion 110.

As a result, one of the inventive concepts is that the orthopedic precast 100 forming the resultant orthosis 195 will have (1) one or more strands of a first (thermoplastic) material interwoven with similar strands of a different material, which upon heating, partially melt and therefore fuse together without significant change in the structure of the interwoven components to form rigid components (e.g., pulley members $160_1$-$160_6$), and (2) one or more interwoven strands of a second (non-thermoplastic) material that remain flexible upon heating and cooling. The strands of the second material do not melt or melt an insubstantial amount at the temperature used to melt the thermoplastic materials forming the first portion 110, collectively form the edge portions 120 and 122. Accordingly, the terms "insubstantial" and "substantial" are used herein in that context as to the amount of thermoplastic material melting to change a portion of the precast of the orthosis into a rigid or semi-rigid state.

Referring to FIG. 2, an exemplary embodiment of an orthopedic precast 200, which can be heated and cooled to produce an articulated ankle-foot orthosis (AFO) configured to restrict movement of lower leg of a patient relative to the foot, is shown. Interwoven as a single, collective unit, the orthopedic precast 200 includes a plurality of interwoven portions, including a first interwoven portion 210, a second interwoven portion 220, a third interwoven portion 230, and a fourth interwoven portion 240. Each of the interwoven portions 210, 220, 230 and 240 comprises strands of material interwoven together to form a flexible (fabric-based) version of the resultant AFO. These strands of material may include thermoplastic material that, upon activation (e.g., heated until reaching a prescribed melting temperature), melts, diffuses and cools to form a rigid or semi-rigid regions of the resultant AFO. An interwoven fastening element 250 may be created to provide a removable coupling between the third interwoven portion 230 and the fourth interwoven portion 240, which form flexible portions of the resultant AFO.

Figures 2A, 2B:
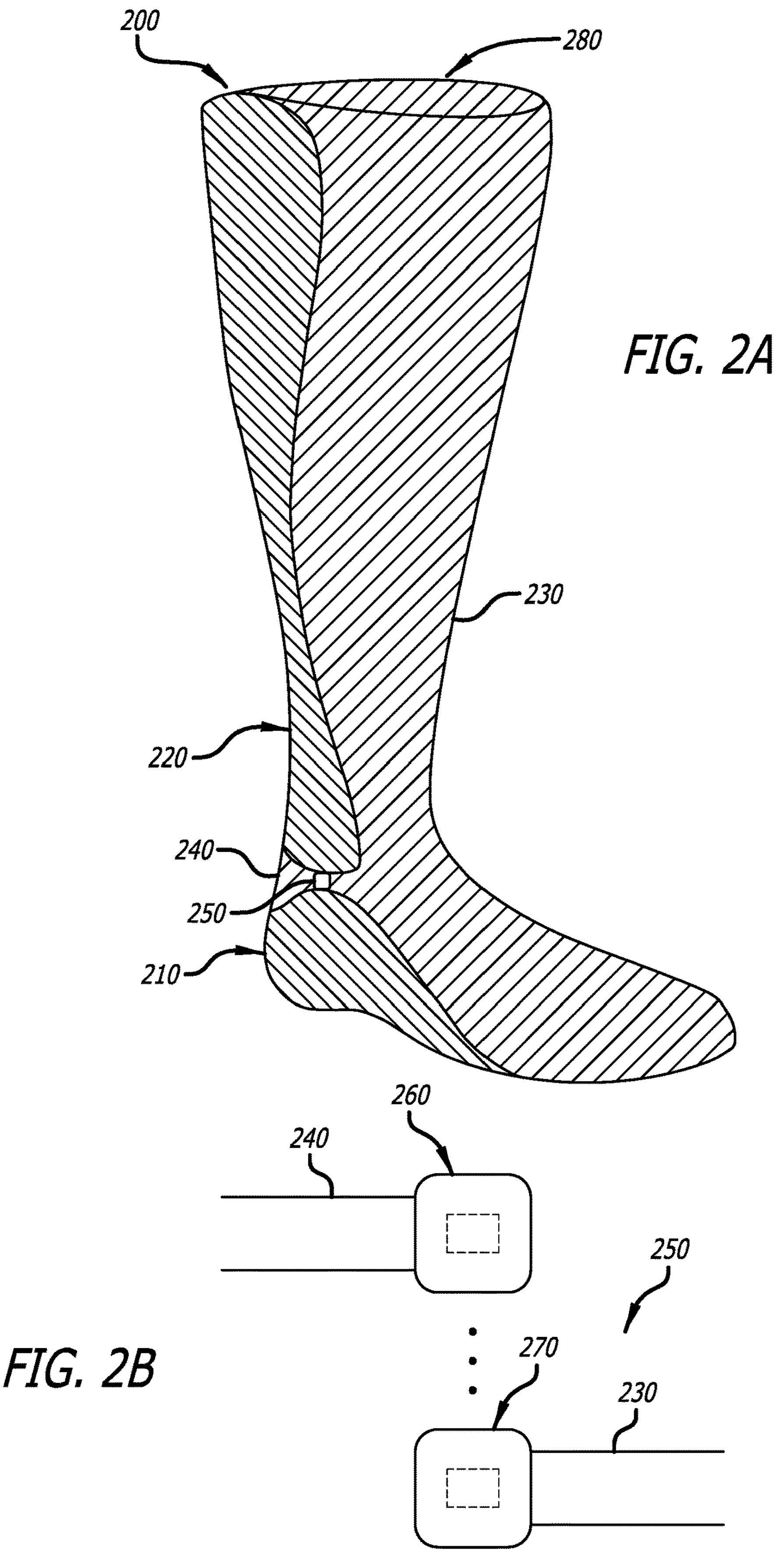
FIG. 2A is a perspective view of an exemplary embodiment of an orthopedic precast of a leg-ankle-foot orthosis with an interwoven, integrated fastening element.
FIG. 2B is a perspective view of an exemplary embodiment of the interwoven, integrated fastening element of FIG. 2A.

For example, as shown in FIG. 2A, the first interwoven portion 210 is configured to operate, upon transformation into a leg-ankle-foot orthosis, as a lower shell portion (e.g., foot plate), and a second interwoven portion 220 is configured to operate, upon transformation into the leg-ankle-foot orthosis, as an upper shell portion (e.g., calf section). The first and second interwoven portions 210 and 220 are at least partially coupled together via by a third interwoven portion 230 configured to operate as a first flexible portion and/or a fourth interwoven portion 240 configured to operate as a second flexible portion. The fourth interwoven portion 240 is arranged to separate the first interwoven portion 210 from the second interwoven portion 220, and thereby, separate the resultant upper and lower shell portions forming the leg-ankle-foot orthosis.

The interwoven fastening element 250 may feature complementary fastening elements both interwoven as a part of orthopedic precast 200. Alternatively, one of the fastening elements for the interwoven fastening element 250 may be interwoven as part of the orthopedic precast 200 while a fastening element complementary to that interwoven fastening element may be attached as a post-production element.

Referring now to FIG. 2B, a perspective view of an exemplary embodiment of the interwoven, integrated fastening element 250 of FIG. 2A is shown. Herein, the interwoven fastening element 250 features a first fastening element 260 and a second fastening element 270. The first fastening element 260 is formed as part of the fourth interwoven portion 240, namely layered strands of thermoplastic material that is arranged so that, upon heating toward a melting temperature of the thermoplastic material (e.g., a temperature that causes melting without destruction of its form) and subsequent cooling, form a male or female fastener. Similarly, the second fastening element 270 is formed as part of the third interwoven portion 230, which overlays or underlays a portion of the fourth interwoven portion 240 forming the first fastening element 260.

More specifically, the second fastening element 270 is formed by layered strands of thermoplastic material that is arranged, upon heating toward a melting temperature of the thermoplastic material (e.g., a temperature that causes melting without destruction of its form) and subsequent cooling, to form a female or male connector complementary to the first fastening element 260. Hence, the interweaving of strands of thermoplastic material to form components, namely fastening elements 260 and 270, avoid the labor-intensive process of sewing, knitting, or weaving certain fasteners into the resultant AFO.

According to one embodiment of the disclosure, other than at a prescribed locations (e.g., location of first fastening element 260), the fourth interwoven portion 240 may be elastic to provide different degrees to tension to the Achilles tendon of the patient.

In a corresponding precast 200, the second interwoven portion 220 and the third interwoven portion 230 cooperate to support posterior and anterior parts of the lower leg, respectively. The second interwoven portion 220 and the third interwoven portion 230 are oriented lengthwise along a tube 280. In this configuration, the third interwoven (flexible) portion 230 simplifies the donning process for the orthosis, while the second interwoven (shell) portion 220 is manufactured to account for dorsiflexion, plantarflexion, inversion, and eversion stability at the ankle.

Alternatively, it is contemplated that each of the fastening elements 260 and 270 may be accomplished by interweaving in silicone or even cotton material at this junction in the garment. The materials would not increase rigidify during heating, but rather, would form an articulation with a rigid shell portion formed by an upper shell portion (e.g., calf section) associated with the second interwoven portion 220. The third interwoven portion 230 may be formed of nylon/elastic material interwoven together to operate in connect with the shell portion after heating.

Figure 3:
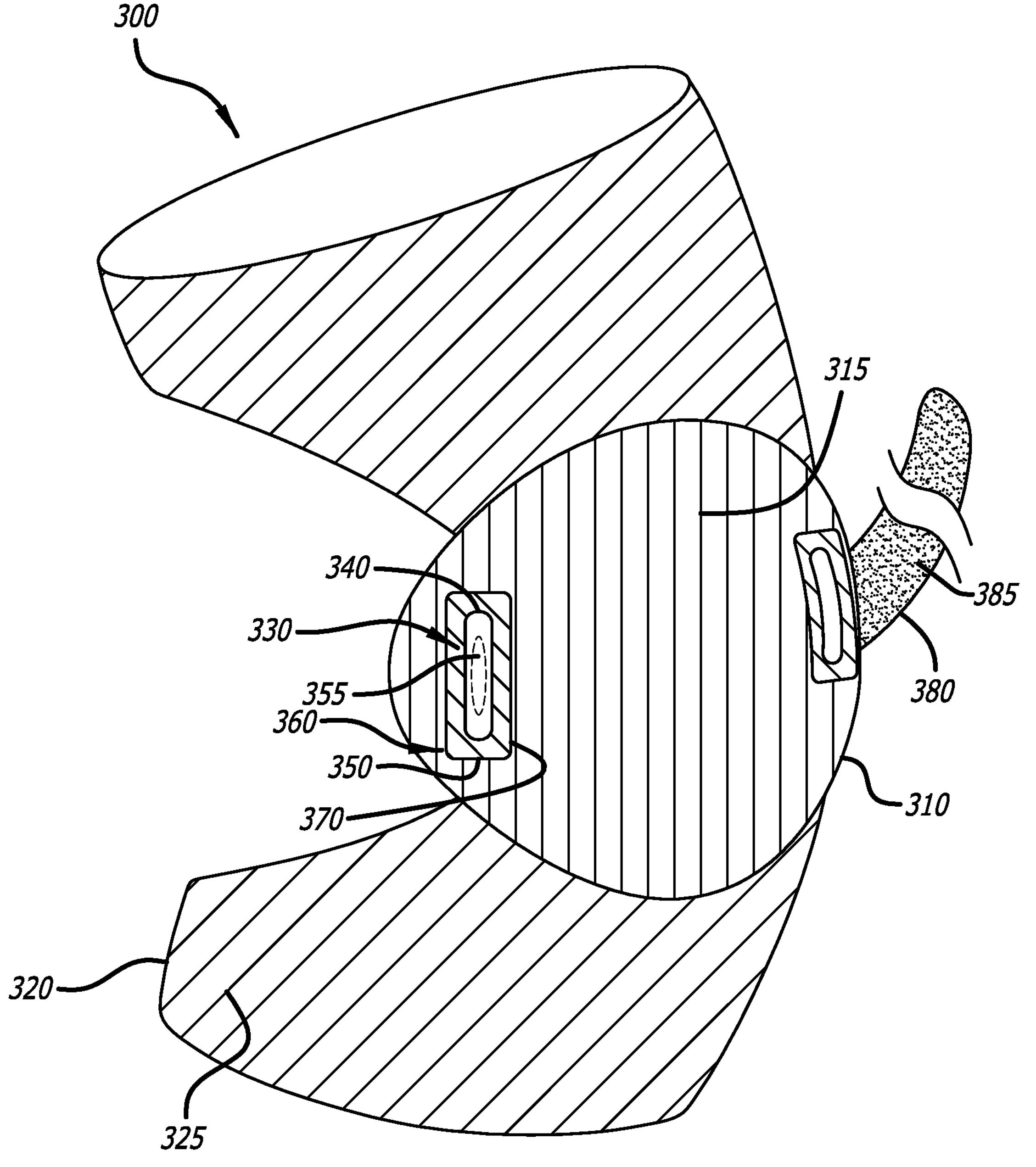
FIG. 3 is a perspective view of an orthopedic precast of a knee protection orthosis with a hardened knee pad and integrated strap guides.

Referring to FIG. 3, a perspective view of an orthopedic precast 300 that produces a knee protection orthosis with a hardened knee pad and integrated strap guides after the strands of material forming the orthopedic precast 300 experience a phase change. Herein, the orthopedic precast 300 featuring at least a first interwoven portion 310, a second interwoven portion 320, and a third interwoven portion 330 situated at selected locations of the first interwoven portion 310. Herein, the third interwoven portion 330 may feature a thermoplastic material 350 with a melting temperature lower than thermoplastic material 315 at least partially forming the first interwoven portion 310. The first interwoven portion 310 includes the thermoplastic material 315 with a lower melting temperature than material 325 forming the second interwoven portion 320. Of course, it is contemplated that the contemplated that, in lieu of thermoplastic material 350, third interwoven portion 330 be interwoven silicone.

Based on this precast structure, the heating of the orthopedic precast 300 to a temperature at or above a lower range of the melting temperature (Tmelt) of the thermoplastic material 315 included as part of the first interwoven portion 310 would cause the following: (a) at least partial melting of the thermoplastic material 315 within the first interwoven portion 310, and (b) complete melting (or incineration) of the thermoplastic material 355 associated with the third interwoven portion 330 to create a strap slot 340. As a result, a framework for a removable knee/elbow protective orthosis is produced from the precast 300, where the first interwoven portion 310 transitions into a rigid shell portion and the second interwoven portion 320 may remain in a flexible or even elastic construction.

As further shown in FIG. 3, the orthopedic precast 330 may include an interwoven component 360, which includes a layering of strands of thermoplastic material 370 similar to the thermoplastic material 315 (e.g., a melting temperature approximately equal to Tmelt). The layering of a first collection of strands of thermoplastic material 370 forms a first strap guide 360 that is arranged to encourage a strap to be directed toward a back of the resultant knee protection orthosis 300.

Thereafter, a strap 380 may be included as a post-production element by anchoring circumvent a patient's knee area and looping a first end of the strap 380 for insertion through at least the strap slot 340. Toward a second end of the strap 380, a fastener (e.g., a hook fastener of a hook & loop fastening mechanism) may be attached to an outer surface 385 of the strap 380 and complementary to a fastener (e.g., unbroken loop (UBL) material for the hook & loop fastening mechanism) positioned toward the first end of the strap 380.

Figure 4A:
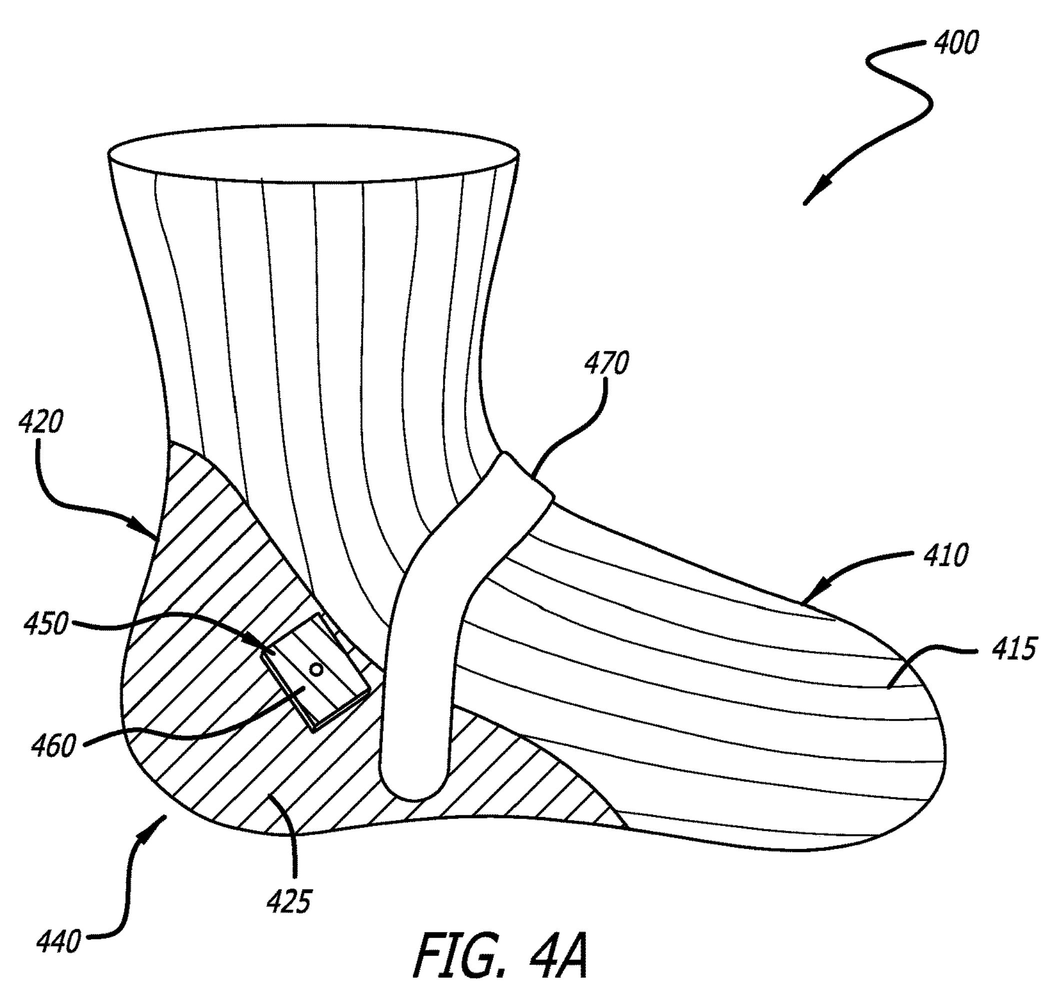
FIG. 4A is a perspective view of an exemplary embodiment of an orthopedic precast for transition into a resultant heal-protective orthosis with an integrated female fastener.

Referring now to FIG. 4A, a perspective view of an exemplary embodiment of an orthopedic precast 400 for transition into a foot orthosis with an integrated fastener 450 is shown. Herein, the orthopedic precast 400 features a first portion 410 and a second portion 420. The second portion 420 features material interwoven with strands of thermoplastic material 425 to form a rigid heal-protective element 440 after the orthopedic precast 400 transitions into the foot orthosis. The strands of thermoplastic material 425 have a melting temperature that is lower than the melting temperature of the interwoven materials 415 forming the first portion 410.

Additionally, the second interwoven portion 420 may include materials other than the strands of thermoplastic material 425 to increase rigidity such as carbon, glass, or other rigid fibers. Also, the fastener 450 may be interwoven as part of the second interwoven portion 420. In particular, multiple layers of strands of thermoplastic material 460 may be interwoven on base layer(s) of the thermoplastic material 425 to provide depth and a construction resembling the fastener 450. Upon activation, namely heating of the second interwoven portion 420 of the orthopedic precast 400 to a temperature that causes melting of the thermoplastic material 460 without destruction of its form and melting of the strands of thermoplastic material 425 of subsequent cooling, the fastener 450 is formed.

Figure 4B:
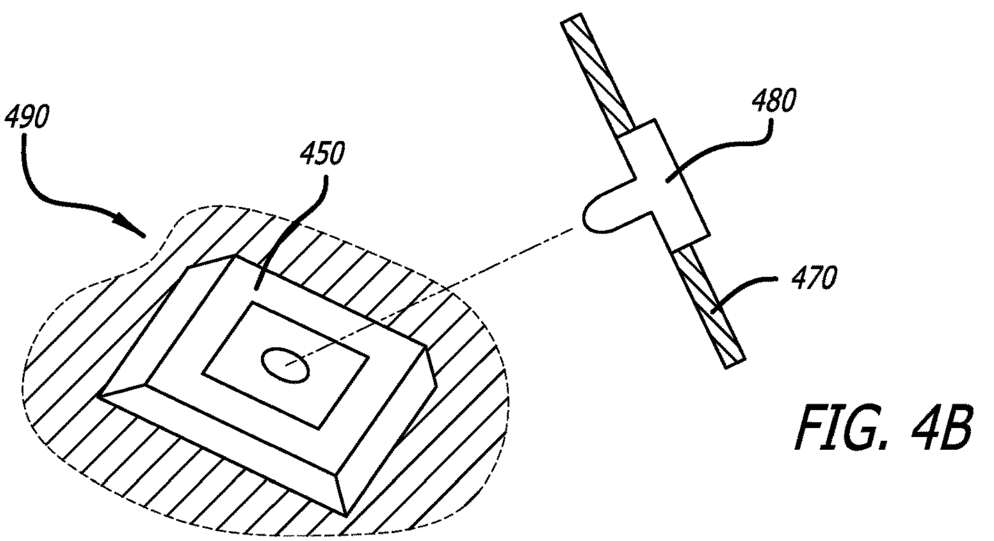
FIG. 4B is a perspective view of a fastening element featuring the integrated female fasteners and a male fasteners for a strap being part of the resultant heal-protective orthosis.

As further shown in FIG. 4A, the first portion 410 may include Kevlar™ or other material having both high levels of strength and flexibility. A strap 470, formed of an integrated non-thermoplastic material, may be used to assist in retaining the orthopedic precast 400 on a lower limb and foot of a patient (not shown). The strap 470 may include a fastener 480, which is complementary to the fastener 450 formed in the second interwoven portion 420 of the orthopedic precast 400 as an integrated fastener of the resultant foot orthosis 490 as shown in FIG. 4B.

Referring now to FIG. 5, a perspective view of an exemplary embodiment of a post-operative shoe precast 500 configured with interwoven, integrated eyelets (e.g., right side eyelets 510) positioned within an interwoven region 520 of the post-operative shoe precast 500. The interwoven region 520 is located above a foot plate 530 as shown. The eyelets 510, the interwoven region 520 and the foot plate 530 may be formed with strands of thermoplastic material as described herein. The eyelets 510 includes one or more additional, interwoven strands of thermoplastic material beyond the strands of thermoplastic material forming the interwoven region 520. The remainder of the post-operative shoe precast 500 (e.g., a second interwoven portion 540) features soft fabric, padding and/or other material.

When areas surrounding the interwoven region 520 of the post-operative shoe 500 are heated to a prescribed temperature (e.g., near, at, or exceeding the melting temperature of the thermoplastic material without destruction of its form) and cooled, the eyelets 510 are formed in the post-operative shoe with greater rigidity than a shell portion formed by the interwoven region 520. This increased rigidity may be due to different thermoplastic material, thicker strands of thermoplastic material, a tighten interweaving pattern that features a greater amount of thermoplastic material, as described below. Also, when heated, the foot plate 530 and portions of the ankle area become rigid to immobilize and protect the patient's foot. The remainder of the post-operative shoe (e.g., second knitted portion 540) retains its flexible characteristics.

IV. Illustrative Phase Transitions for Interwoven Components

Referring now to FIGS. 6A-7D, embodiments of portions of components associated with an orthopedic precast (hereinafter, "interwoven components"), which feature multiple layers of interwoven material, are described. According to these embodiments, each interwoven component may include multiple interwoven layers of materials. Interwoven components with multiple material layers may be accomplished through a number of techniques, including complex multi-layering interweaving processes, separate interwoven portions positioned on each other and attached together, or a precast with a single layer of interwoven materials that is folded over itself or another precast to form multiple layered interwoven portions.

Referring to FIG. 6A, an exemplary embodiment of an interwoven component 600 of an orthopedic precast, which includes a second interwoven portion 620 featuring one or more strands of a second material 625 with a lower melting point than one or more strands of a first material 615 associated with a first interwoven portion 610, is shown. For this illustrative embodiment, different materials 615 and 625 may be layered when forming the interwoven component 600. For example, the second material 625 may be partially melted, without destruction of its form or function, when a prescribed temperature is applied to provide rigidity after cooling while the first material 615, upon which the interwoven component 600 is mounted, may experience no or lesser phase change (e.g., no change from solid to partial liquid phase that is cooled to re-solidify).

As with all examples herein, where the second material 625 associated with the second interwoven portion 620 constitutes a thermoplastic material with a lower melting point than the first material 615 associated with the first interwoven portion 610, it is contemplated that the difference in melting points can arise because the first material 615 has no melting point or a melting point considerably greater than the melting point of the second material 625. For example, the first material 615 may be a nylon or Kevlar™ for example.

Referring now to FIG. 6B, an exemplary embodiment of a portion of the interwoven component 600 shown in FIG. 6A is shown, following heating at or above the lower range of the melting point of the thermoplastic material 625 of the second interwoven portion 620. Upon the application of heat at or above the lower range of the melting point of the thermoplastic material 625, one or more portions 640 of the thermoplastic material 625 partially melts. The heat may be provided by a heat source 630, including but not limited to a heater that produces a heated ambient environment, a heater that produces heated air flow, or a heater that produces heated steam. After cooling, the thermoplastic material 625 solidifies to retain its form as a rigid or semi-rigid fastener or other component formed as part of the second interwoven portion 620.

Referring to FIG. 7A, an exemplary embodiment of a portion of an interwoven component 700 of an orthopedic precast having a second interwoven portion 722 configured with a higher concentration of a thermoplastic material 721 than a first interwoven portion 710 is shown. According to this embodiment of the disclosure, upon applying heat at or above the lower range of the melting point of the thermoplastic material 721, both the first interwoven portion 710 and the second interwoven portion 722 may experience a partial phase change caused by partially melting of the thermoplastic material 721.

As shown, the second interwoven portion 722 may experience a greater volume of melted thermoplastic material 721 due to its higher concentration level. Therefore, after cooling, both the first interwoven portion 710 and the second interwoven portion 722 may solidify, with the second interwoven portion 722 becoming more rigid than the first interwoven portion 710 due to the higher concentration of thermoplastic material. As a result, the orthosis produced by the interwoven component 700 may feature different layers with an outer layer associated with the second interwoven portion 722 having a higher level of rigidity than an inner layer associated with the first interwoven portion 710.

Referring now to FIG. 7B, an exemplary embodiment of a portion of an orthopedic interwoven component 704, which features a first interwoven portion 714 configured with a first interweaving pattern 715 and a second interwoven portion 724 configured with a second interweaving pattern 725 different from the first interwoven portion 714, is shown. Herein, for this illustrative example, the second interweaving pattern 725 of a thermoplastic material is tighter than the first interweaving pattern 715 of the thermoplastic material. According to this interwoven component architecture, upon applying heat at or above the lower range of the melting point of the thermoplastic material, both the first interwoven portion 714 and the second interwoven portion 724 may experience a partial phased change caused by partially melting of the thermoplastic material. However, given this second interweaving pattern 725 features a greater amount of thermoplastic material over a prescribed distance or area than the first interweaving pattern 715, the second interwoven portion 724 may experience a greater volume of melted thermoplastic material. As a result, after cooling, the second interwoven portion 724 may be formed as a shell portion with greater rigidity and the first interwoven portion 714 may also be formed as a shell portion. Hence, different types of interweaving patterns may be used to influence the rigidity of a resultant shell portion(s) of an orthosis.

Referring to FIG. 7C, an exemplary embodiment of an interwoven component 706 of an orthopedic precast having a first interwoven portion 716 configured with thinner strand(s) 717 of a thermoplastic material than the second interwoven portion 726 is shown. Stated differently, the second interwoven portion 726 is configured with thicker strand(s) 727 of the thermoplastic material than the strand(s) 717 of the thermoplastic material in the first interwoven portion 716.

According to this interwoven component architecture, where the same thermoplastic material is utilized in the first interwoven portion 716 and the second interwoven portion 726, upon applying heat at or above the lower range of the melting point of the thermoplastic material, both the first interwoven portion 716 and the second interwoven portion 726 may experience a partial phase change caused by partially melting of the thermoplastic material. However, given that the strand(s) 727 of the thermoplastic material within the second interwoven portion 726 is(are) thicker than the strand(s) 717 of the thermoplastic material within the first interweaving pattern 715, during a melting process, a greater amount of thermoplastic material within the second interwoven portion 726 may be melted.

As a result, after cooling, the second interwoven portion 726 would be formed as a shell portion with greater rigidity than a shell portion formed by the first interwoven portion 716. Hence, different types of strand thicknesses may be used to influence the rigidity of a resultant shell portion of an orthosis.

Referring to FIG. 7D, an exemplary embodiment of an interwoven component 708 of an orthopedic precast having a second interwoven portion 728 configured with a plurality of layers that include strands of a thermoplastic material, where the number of layers of the second interwoven portion 728 exceed a first interwoven portion 718. According to this interwoven component architecture, upon applying heat at or above the lower range of the melting point of the thermoplastic material, the second interwoven portion 728 would experience a phase change caused by partially melting of the thermoplastic material. However, given this second interwoven portion 728 has a greater amount of thermoplastic material over a prescribed distance or area than the first interwoven portion 718 and the transfer of heat may be diminished as heat transfers into the first interwoven portion 718 via the second interwoven portion 728, the second interwoven portion 728 may experience a greater volume of melted thermoplastic material. As a result, after cooling, the second interwoven portion 728 would be formed as a shell portion with greater rigidity and the first interwoven portion 718. Hence, multiple layers of thermoplastic material may be used to influence the rigidity of a resultant shell portion of an orthosis.

These and other products may be formulated in accordance with selected positioning of interwoven portions with thermoplastic materials, heating, and subsequent cooling to achieve rigidity of these interwoven portions.

It is still further contemplated instead of thermoplastic strands (e.g., threads, yarns, etc.) being heated and then cooled to form a shell portion, material could be used in the strands that is hardened by polymerization, with the polymerizing energy coming from ambient or artificial light, an oxidizing or reducing agent, or any other suitable energy source.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. An orthopedic precast operating as an initial structure used in producing an orthosis, comprising:
- a first portion with layers of material interwoven with thermoplastic material to form one or more components for use in fitting of the orthosis to a patient upon activation of the thermoplastic material to transition from a flexible material to a rigid material; and
- a second portion with a second layer of material interwoven with the thermoplastic material, wherein the one or more components include one or more pulley members.

2. The orthopedic precast of claim 1, wherein the one or more pulley members operate as a pulley system to adjust a lateral sizing of the orthosis.

3. The orthopedic precast of claim 2, wherein the orthosis is a lumbar-sacral orthosis.

4. An orthopedic precast operating as an initial structure used in producing an orthosis, comprising:
- a first portion with layers of material interwoven with thermoplastic material to form one or more components for use in fitting of the orthosis to a patient, each component of the one or more components corresponds to a plurality of strands of the thermoplastic material that are layered to form a structure for the component that, after activation of the plurality of strands of the thermoplastic material, transitions from a flexible state to a rigid state to form the component being part of the orthosis; and
- a second portion with a second layer of material interwoven with the thermoplastic material; and wherein the one or more components include one or more pulley members.

5. The orthopedic precast of claim 4, wherein the one or more pulley members operate as a pulley system to adjust a lateral sizing of the orthosis.

6. The orthopedic precast of claim 5, wherein the orthosis is a lumbar-sacral orthosis.

7. The orthopedic precast of claim 4, wherein the activation of the plurality of strands of the thermoplastic material includes applying heat to partially melt the plurality of strands of the thermoplastic material that, after cooling, transition from the flexible state to the rigid state in which the one or more components correspond to one or more fasteners.

8. An orthopedic precast operating as an initial structure used in producing an orthosis, comprising:
- a first plurality of strands of a thermoplastic material layered and interwoven in a pattern to form one or more components for use in fitting of the orthosis to a patient upon activation of the thermoplastic material to transition from a flexible material to a rigid material; and
- a second plurality of strands of material interwoven with the first plurality of strands of the thermoplastic material, wherein the one or more components include one or more pulley members of a pulley system.

9. The orthopedic precast of claim 8, wherein the one or more pulley members of the pulley system are arranged to assist in adjusting a lateral sizing of the orthosis.

10. The orthopedic precast of claim 9, wherein the orthosis is a lumbar-sacral orthosis.

* * * * *